(12) United States Patent
Ziegler et al.

(10) Patent No.: US 8,863,790 B2
(45) Date of Patent: Oct. 21, 2014

(54) STERILIZATION WITH β-RADIATION

(75) Inventors: Manfred Ziegler, Ruderting (DE); Jochen Krueger, Thalmassing (DE)

(73) Assignee: Krones AG (DE)

( * ) Notice: Subject to any disclaimer, the term of this patent is extended or adjusted under 35 U.S.C. 154(b) by 1263 days.

(21) Appl. No.: 12/665,297

(22) PCT Filed: Jun. 25, 2008

(86) PCT No.: PCT/EP2008/058070
§ 371 (c)(1),
(2), (4) Date: Mar. 1, 2010

(87) PCT Pub. No.: WO2009/000850
PCT Pub. Date: Dec. 31, 2008

(65) Prior Publication Data
US 2010/0193069 A1 Aug. 5, 2010

(30) Foreign Application Priority Data
Jun. 26, 2007 (DE) .......................... 10 2007 029 567

(51) Int. Cl.
| | |
|---|---|
| *B65B 1/04* | (2006.01) |
| *B65B 55/02* | (2006.01) |
| *B67C 7/00* | (2006.01) |
| *A61L 2/24* | (2006.01) |
| *A61L 2/08* | (2006.01) |
| *B65B 55/08* | (2006.01) |
| *B67C 3/22* | (2006.01) |

(52) U.S. Cl.
CPC ............... *A61L 2/087* (2013.01); *B67C 7/0073* (2013.01); *B67C 2003/228* (2013.01); *B67C 7/004* (2013.01); *A61L 2/24* (2013.01); *B65B 55/08* (2013.01)
USPC ................... 141/92; 141/11; 141/69; 141/89; 141/91; 141/97; 141/131; 53/425

(58) Field of Classification Search
USPC ............... 141/11, 69, 89, 91, 92, 97, 98, 129, 141/131; 53/425, 426, 428, 467, 473, 266.1
See application file for complete search history.

(56) References Cited

U.S. PATENT DOCUMENTS 3,780,308 A 12/1973 Nablo ........................... 250/492
4,934,129 A * 6/1990 Hoffman et al. ................ 53/443

(Continued)

FOREIGN PATENT DOCUMENTS

| | | | |
|---|---|---|---|
| CA | 1006327 | 3/1977 | |
| EP | 0340411 | 3/1989 | .............. B65B 55/04 |
| FR | 2 255 916 | 12/1973 | ................ A61L 1/00 |
| JP | S50050187 | 5/1975 | .............. B65B 31/02 |
| JP | 2007126168 | 5/2007 | ................ A61L 2/08 |
| JP | 2007536174 | 12/2007 | ................ A61L 2/08 |
| WO | WO 04/000100 | 12/2003 | |
| WO | WO 2005/108278 | 11/2005 | ................ B67C 7/00 |

OTHER PUBLICATIONS

Japanese Office Action issued for JP2010513900 (with English translation), dated Sep. 25, 2012 (4 pgs).
International Search Report dated Oct. 7, 2008.
Chinese Office Action issued in corresponding application No. 200880021868.2, dated Aug. 21, 2012 (7 pgs).

*Primary Examiner* — Timothy L Maust
(74) *Attorney, Agent, or Firm* — Hayes Soloway P.C.

(57) ABSTRACT

An apparatus for filling containers, has an entrance through which open containers can be introduced into the apparatus, including at least one transport device which conveys the containers along a predefined transport path, and an exit via which the containers can be discharged from the apparatus. The speed at which the transport device conveys the containers is variable, and the apparatus comprises at least one filling device which fills the containers at least partially with a liquid medium on the transport path between the entrance and the exit. The apparatus includes a housing, and arranged in the interior of the housing is at least one sterilization device in the form of a β-radiation unit which sterilizes components of the apparatus.

18 Claims, 2 Drawing Sheets

(56) References Cited

U.S. PATENT DOCUMENTS

| | | | |
|---|---|---|---|
| 4,944,132 A | 7/1990 | Carlsson et al. | 53/167 |
| 6,189,292 B1 * | 2/2001 | Odell et al. | 53/425 |
| 6,343,628 B2 * | 2/2002 | Reinecke | 141/165 |
| 6,436,343 B1 * | 8/2002 | Bechini | 422/28 |
| 6,929,040 B2 * | 8/2005 | Py | 141/329 |
| 7,520,108 B2 * | 4/2009 | Kristiansson et al. | 53/426 |
| 7,556,066 B2 * | 7/2009 | Py | 141/85 |
| 7,739,859 B2 | 6/2010 | Colato et al. | 53/426 |
| 2007/0023767 A1 | 2/2007 | Ogihara et al. | 422/28 |

* cited by examiner

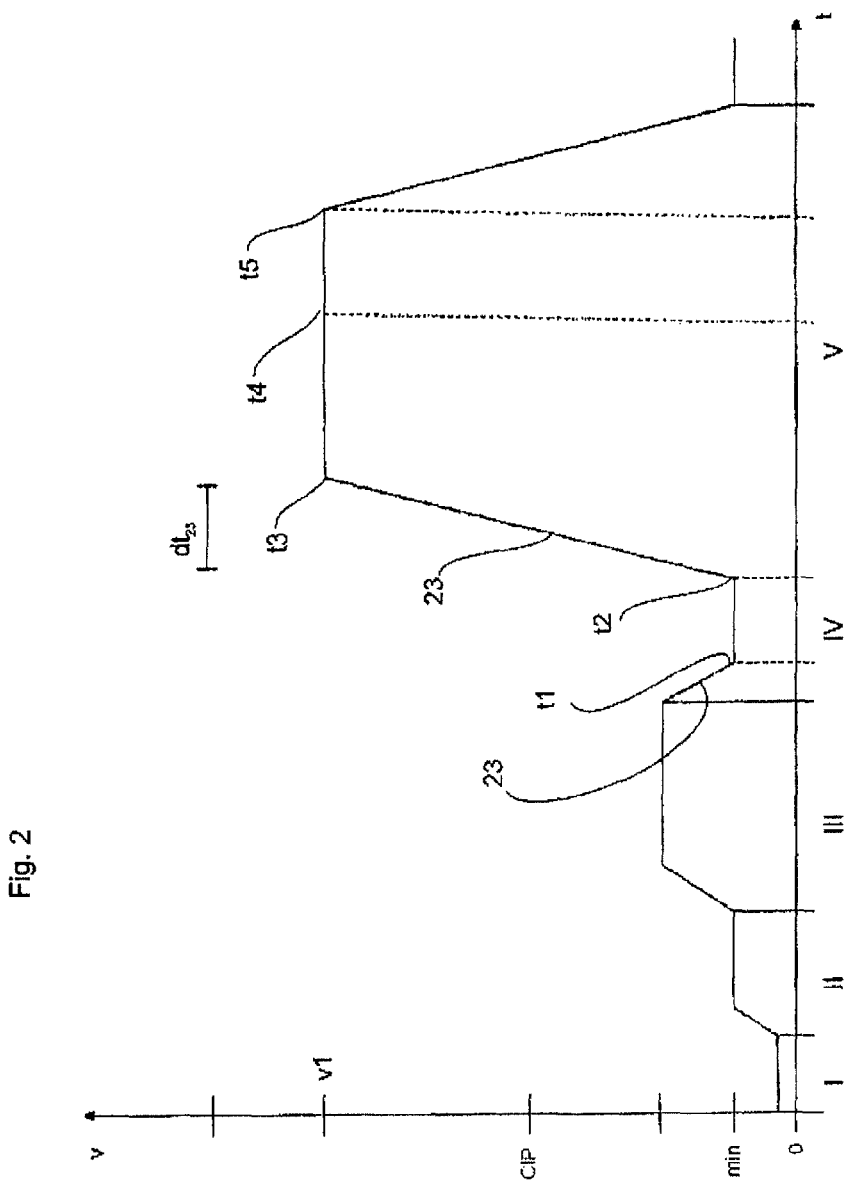

STERILIZATION WITH β-RADIATION

BACKGROUND OF THE INVENTION

The object of the present invention is therefore to provide an apparatus and a method for filling containers, which allow a high degree of sterilization of the filled containers.

SUMMARY OF THE INVENTION

The object of the present invention is therefore to provide an apparatus and a method for filling containers, which allow a high degree of sterilization of the filled containers. This is achieved by an apparatus according to claim 1, an installation according to claim 11 and a method for treating containers according to claim 14. Advantageous embodiments and further developments form the subject matter of the dependent claims.

An apparatus according to the invention for filling containers comprises an entrance through which open containers can be introduced into the apparatus. Also provided is a transport device which conveys the containers along a predefined transport path downstream of the entrance, and also provided is an exit via which the containers can be discharged from the apparatus. The speed at which the transport device conveys the containers is variable, and also provided is at least one filling device which fills the containers at least partially with a liquid medium on the transport path between the entrance and the exit.

According to the invention, the apparatus comprises a housing and arranged in the interior of this housing is at least one sterilization device in the form of a β-radiation unit and also for example X-ray radiation, which sterilizes components of the apparatus. Preferably, the housing is a closed housing so as to prevent β-radiation and for example also X-ray radiation from escaping from the apparatus. The transport device is particularly preferably a transport carousel, on which there is arranged a plurality of filling devices which fill the containers with the beverage. Furthermore, a plurality of transport devices, for example in the form of transfer starwheels or the like, are preferably arranged inside the apparatus. The β-radiation unit or the β-emitter, due to the emission of β-radiation, sterilizes components of the apparatus and in this way keeps the apparatus sterile, in particular even during continuous operation.

Preferably, the intensity of this at least one β-radiation unit is controllable. Controllable is understood here to mean that the radiation unit is switchable not only between an ON state and an OFF state but rather is controllable in at least two different intensity levels and preferably is continuously variable between a minimum intensity value and a maximum intensity value. For example, it is possible to vary the acceleration voltage in an acceleration tube of the β-radiation unit in order to vary the intensity of the β-radiation.

In one preferred embodiment, the apparatus comprises a control unit which is configured in such a way that it controls the intensity of the at least one β-radiation unit as a function of an operating parameter of the apparatus.

Preferably, the operating parameter is the transport speed of the transport device. In general, a certain dose of β-radiation is necessary in order to achieve efficient sterilization of the respective components. If the machine speed is curbed, the individual components are located in the irradiation region of a given β-radiation unit for a longer period of time. In this case, therefore, preferably the intensity of the relevant β-radiation unit is reduced. In this way, a required dose of β-radiation, which if possible should neither be undershot nor exceeded, can be achieved even at different transport speeds.

In a further preferred embodiment, the operating parameter of the apparatus is an open state of a barrier device for the containers which is provided upstream of the apparatus. By way of example, in the event of failure of other units of a complete installation, it may happen that the flow of containers must be interrupted. If such a barrier device is closed and thus no further containers enter the apparatus, then in the preferred embodiment the corresponding radiation power is reduced as soon as there are no longer any containers in the apparatus, and thus it is possible that the required cooling power for the β-radiation unit can likewise be reduced. In this case, however, the control device causes a lowering of the intensity or radiation power to take place only when there are no longer any containers within the apparatus. This prevents a non-uniform sterilization of certain components, which may in turn have an effect on the containers themselves.

In one preferred embodiment, the components irradiated by the β-radiation unit are selected from a group of components which contains transport starwheels, fittings, gripping devices for the containers and the like. It is thus pointed out that it is not the containers themselves that are irradiated with β-rays by the apparatus according to the invention, but rather only the components which treat the containers.

In a further advantageous embodiment, the at least one β-radiation unit is provided and/or arranged in such a way that the β-ray coming from the β-radiation unit is not directed onto the containers during transport of the containers. For example, a cover sheet plate may be provided which is arranged over the transported containers, and the radiation unit sterilizes only regions above this cover sheet plate. Furthermore, the β-radiation units may be arranged in such a way that a sterilization takes place below the transport path of the containers and in particular also below the containers themselves.

Furthermore, the β-radiation units may be provided in regions of the transport device at which no containers are located at any point in time. If, for example, transport starwheels are used as the transport device, then usually a handover starwheel is provided upstream of these transport starwheels and transfers the containers to the transport starwheel, and a pick-up starwheel is provided downstream of the transport starwheel and picks up the containers from the transport starwheel. In the circumferential direction of the transport starwheel, usually a certain angular range is provided in which the gripping devices for the containers are always empty, that is to say in which no containers are located at any point in time. In one preferred embodiment, the β-radiation units are arranged in such a region and/or are arranged in such a way that only such a region is irradiated. Some foodstuff guidelines, such as for example guidelines from the US FDA (Food and Drugs Administration) stipulate that rays, such as β-rays in this case, must not come into contact with the actual beverage, since contamination of the beverage is possible.

This also applies to droplets of the beverage which may still enter the containers.

However, by virtue of special embodiments of the β-radiation units, it is also possible to ensure that the emitted radiation profile does not come into contact with the containers. For instance, geometrically precisely defined "radiation lobes" can be generated by specially adapted apertures of the β-radiation unit. In this case, account must be taken of the fact that the β-radiation is attenuated by the medium, for example sterilized air or nitrogen or a noble gas, and thus a precise profile of this "radiation lobe" can be predefined also by taking account of these components and the arrangement of the sterilization device itself.

In a further preferred embodiment, the apparatus is arranged in a clean chamber and this clean chamber is filled with a gas selected from a group of gases which contains noble gases, nitrogen, sterilized air and the like. Preferably, said gas is at superatmospheric pressure in the area surrounding the apparatus.

In a further preferred embodiment, a plurality of β-radiation units are provided which are arranged in a stationary manner. By providing stationary radiation units, it is possible in a particularly advantageous manner to achieve the situation whereby the containers do not come into contact with the β-radiation or the electron beam.

The present invention also relates to an installation for treating containers, comprising an apparatus of the type described above and a sterilization device which is arranged upstream of this apparatus and which sterilizes the containers. It is pointed out here that, in said sterilization device, the containers themselves are sterilized internally and externally and thus arrive at the apparatus in a completely sterilized manner. The terms upstream and downstream are defined here with reference to the transport direction of the containers.

Preferably, the sterilization device comprises at least one conveying device which conveys the containers through the sterilization device.

Preferably, the drives of the transport device and of the conveying device can be controlled independently of one another. It is thus possible to operate the transport device and the conveying device independently of one another. In principle, it is customary in the prior art to synchronize a plurality of drives with one another and thus to allow block operation. In this preferred embodiment, this synchronization is at least at times suspended. As will be explained in more detail below, this suspending of the synchronization is particularly beneficial for start-up processes. Separate drives are preferably provided for the conveying device (of the sterilization device) and the transport device, and particularly preferably drives in the form of servo motors.

Preferably, however, it is also possible to synchronize the drive of the transport device at times with the drive of the conveying device. This is particularly beneficial for the normal production mode.

The present invention also relates to a method for treating containers. In a first method step, open containers are fed into an apparatus for filling containers and in particular into an apparatus of the type described above. In one method step, the containers are transported and are filled during this transport. Finally, the filled but preferably still open containers are discharged from the apparatus for filling containers.

According to the invention, the components of the apparatus for filling containers are sterilized by at least one sterilization device during the filling process and this sterilization device comprises at least one β-radiation unit. Preferably, one or several components of the apparatus are sterilized by a plurality of β-radiation units.

Preferably, the intensity of the β-radiation units is controlled as a function of a transport speed of the containers through the apparatus. In the case of a low transport speed, the power of the radiation unit can accordingly be reduced in order to maintain or achieve a certain dose that is required.

Preferably, the apparatus is operated at least at times in an idle mode in which no containers are transported through the apparatus but the transport speed of the apparatus is other than 0, wherein in this idle mode the intensity of at least one β-radiation unit is reduced. It is pointed out that preferably a certain speed of the components, for example of the gripping devices or of the transport starwheels, is maintained even in an idle mode in which no containers are located in the apparatus, in order to ensure that the sterilization continues to take place even during this rest mode. In this way, a high degree of sterilization of the entire apparatus can be maintained even during rest times.

Preferably, the containers are sterilized by a sterilization device prior to filling. In this case, it is particularly preferably possible that, during a start-up mode, the conveying speed at which the sterilization device conveys the containers and the transport speed at which the apparatus transports the containers are matched to one another. For example, it is possible that the transport device of the apparatus is sterilized in the context of a synchronization process at the speed of the conveying device of the sterilization device. In this synchronization process, therefore, blocking is carried out in relation to said sterilization device, wherein this preferably takes place by means of servo technology. This blocking is carried out in the "on-the-fly" mode. As a result, it is possible that an emitter-induced reduction in speed or a so-called first-round start-up takes place for example at the start of production. By virtue of this synchronization mode, it is also possible to carry out a possible product emptying or the like.

Preferably, the matching of the speed of the transport device and of the conveying device takes place for a predefined period of time and this period of time corresponds essentially to a whole-number multiple of the period of time in which the containers are conveyed through one complete revolution in the transport device. If, for example, a transport carousel is used as the transport device, the matching takes place in the period of time in which a certain gripping arm carries out essentially one, two, three . . . or n revolutions. In this way it is ensured that no non-uniform sterilizations take place during this acceleration or matching process. With particular preference, the speed of the transport device is adapted linearly, that is to say the acceleration or slowing process takes place linearly. Since the transport device and thus also the further transport starwheels synchronized therewith move more slowly during the start-up process, a higher dose of β-radiation can be applied thereto. Due to the fact that the slowing is carried out for a given period of time, the sterilization takes place uniformly for all filling stations. In this way, the situation can ultimately be achieved whereby the amount of rejected containers due to said start-up processes is kept small.

BRIEF DESCRIPTION OF THE DRAWINGS

Further advantages and embodiments will emerge from the appended drawings:

In the drawings:

FIG. 2 shows a time/speed diagram for an apparatus according to the invention.

DETAILED DESCRIPTION OF THE INVENTION

Figure 1:
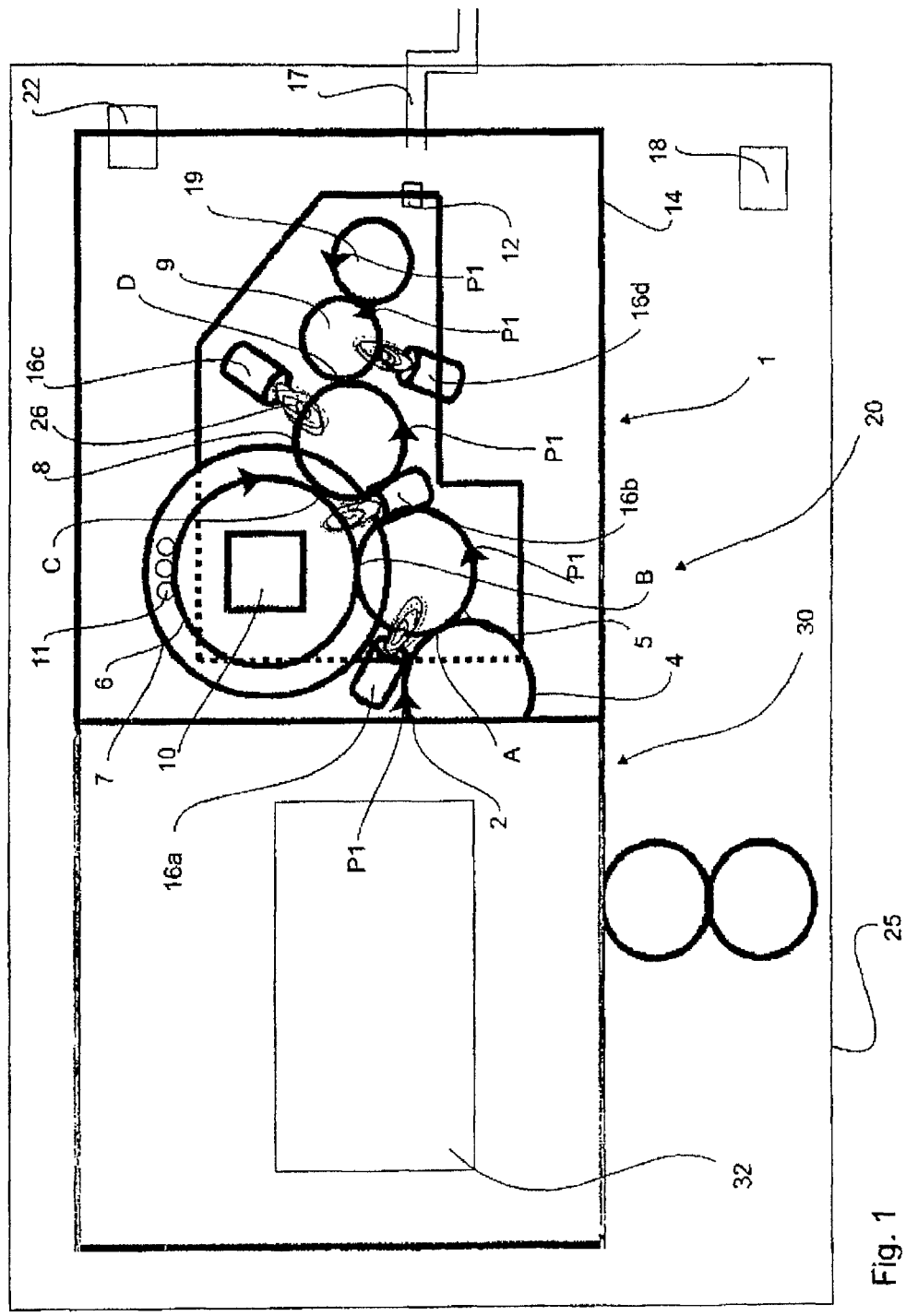
FIG. 1 shows a schematic view of an apparatus according to the invention.

FIG. 1 shows a schematic view of an installation 20 according to the invention for treating containers. This installation 20 comprises an apparatus 1 for filling containers or a filling machine 1. The containers (not shown) are transported through the filling machine 1 from an entrance 2 towards an exit 12 in the direction of the arrows denoted P1. For transporting the containers, use is made of a plurality of transport carousels 4, 5, 8, 9, 19. At each of these transport carousels, gripping devices (not shown) are provided which transfer the containers to the respective next carousel. The apparatus 1 is adjoined by a labyrinth path 17 which prevents radiation from being able to escape from the apparatus 1. Furthermore, the apparatus 1 is adjoined by a closing device (not shown) which closes the containers after they have been filled. Thus the unclosed containers enter the filling machine 1, are filled therein and are then discharged again from the filling machine in the filled but still open state. The individual transport devices 4, 5, 8, 18, 19 must therefore be suitable, for example with regard to their movements, for transporting unclosed, filled containers.

Reference 10 schematically shows the actual filling device which fills the containers. This filling device 10 comprises a plurality of filling elements 11 (shown only schematically) which are arranged on a carousel 6. This carousel 6 is thus the abovementioned transport device 6. These filling elements 11 may be for example nozzles which fill the beverage into the containers. Reference 7 denotes a cover for the transport device 6.

As mentioned above, it is necessary to keep the entire apparatus as sterile as possible even during ongoing operation. For this purpose, use is made of the schematically shown β-radiation units 16a, 16b, 16c, 16d. As shown in FIG. 1, these β-radiation units in each case emit defined radiation beams 26 and/or emit defined radiation doses onto components of the apparatus.

The irradiated components of the apparatuses are for example guide elements, gripping elements, sealing elements and the like. Preferably, however, care must be taken to ensure that the containers themselves and also the beverage that is to be filling into the latter do not come into contact with the β-radiation.

The electron beams and/or β-rays are generated in vacuo in the radiation units 16a-16d and accelerated. The rays then pass through a 10-15 μm thin titanium film, which serves as a window, into the atmosphere region and at the end of their propagation time must still have enough energy to kill spores. The electron beams can be slowed very easily by materials and for example also by air. During this slowing, however, X-ray radiation is produced which in turn requires a considerable screening effort. With particular preference, therefore, a housing 14 is provided which is particularly preferably surrounded by an X-ray-absorbing lining, for example with a lead jacket.

A suction device 22 is also preferably provided for removing by suction any ozone that may be produced. In another alternative variant, it is possible to flush the relevant treatment area within the housing 14 with nitrogen or noble gas. Reference 18 denotes a control device which controls the individual processes.

With particular preference, the β-radiation units comprise exit windows which are at least 5 cm, preferably at least 10 cm and particularly preferably at least 15 cm long. These lengths differ from the lengths of the exit windows of conventional radiation units and are advantageous in the present case for generating the desired radiation profile which is spatially very precisely defined. The exit windows thus have the shape of a slot-shaped aperture. The width of the exit windows lies in a range from 0.1 mm to 1 mm.

With particular preference, the β-radiation units 16a-16d are arranged at those regions along which no containers are conveyed during the production process. By way of example, on the transport device 5, a β-radiation unit 16a is provided in a region along which the containers are not conveyed, since the containers are picked up at a transfer point A and are handed over to the filling machine 10 at a transfer point B.

Here, the containers are guided in the transport device 6 in the counter-clockwise direction and no bottles are therefore conveyed in the counter-clockwise direction between the transfer points B and A.

It is thus possible to clean the transport carousel 5 in this region without contaminating the containers themselves. In a corresponding manner, the β-radiation unit 16b is also arranged in a region between the transfer point B and the transfer point C, along which no containers are conveyed. Since the individual transport devices 4, 5, 8, 9, 19 and also the filling machine 10 move, an efficient overall cleaning can be carried out by the β-radiation units. The irradiation unit 16c and the irradiation unit 16d are also located in each case at regions of the respective transport carousels 9 and 19 along which no containers are conveyed in each case.

Reference 18 denotes a control device which controls both the filling device 10 and the β-radiation units. In this case, preferably the drive of the filling device 10 is synchronized with the drives of the individual transport units 4, 5, 8, 9 and 19.

Reference 30 denotes a sterilization device which serves for sterilizing the containers themselves. As mentioned above, the drive of a conveying device 32, which conveys the containers in the sterilization device 30, and the drive of the transport device of the filling machine 10 can be controlled independently of one another. Reference 25 denotes a housing which surrounds the entire installation. Preferably, an atmosphere of nitrogen, a noble gas or sterile air is located inside this housing 25.

FIG. 2 shows schematically and by way of example a speed profile for an apparatus for filling containers and in particular for the transport devices of this apparatus. Here, the time t is plotted on the ordinate and the speed v of the respective transport devices is plotted on the abscissa. In the first section I, a rest mode takes place. In this segment, the speed could also be zero. However, it is possible to perform a continuous sterilization of the apparatus in the context of very slow ongoing operation for example. During section II, preparation measures may for example be performed, for example an apparatus for closing the containers which is arranged downstream of the apparatus may be filled with closures.

Reference 23 in each case denotes acceleration or slowing sections, in which the transport speed of the apparatus 1 is accelerated or slowed preferably linearly from an initial speed to an end speed.

In section III, the apparatus is prepared for the actual production process (section V). During this period of time it is possible to irradiate the apparatus already with a certain β-radiation dose. The initial power or intensity of the β-radiation units can be reduced, since during this period of time the transport speed is also lower and thus an efficient sterilization of the individual machine components is possible in the same way. During the period of time IV, a synchronization with an upstream sterilization device is prepared.

At the illustrated time t1, a bottle barrier for the containers is still closed and thus no containers yet enter the apparatus 1 or even the sterilization device 30 arranged upstream thereof. At the time t2, the bottle barrier is automatically opened and this means that containers can now enter the sterilization device 30. At the same time, preferably the speed of the apparatus 1 is accelerated and is brought to the production speed v1. Here, this acceleration is carried out by means of servo technology, wherein the time dt23 between the start of the acceleration process (time t2) and the end of the acceleration process (time t3) corresponds to the time in which the transport device 6 of the filling device 10 carries out one complete revolution or whole-number multiples of one revolution.

In the diagram shown in FIG. 2, the speed of the filling device is accelerated. However, it would also be possible that a slowing is carried out between the time t2 and the time t3, depending on the application. From the time t3 onwards, the apparatus 1 runs at its production speed v1. During this period of time, the speed of the filling device is also synchronous with the speed of the upstream sterilization device 30. At the time t4, the bottle barrier is closed automatically, but the speed of the filling device is maintained until the time t5 in order to empty the apparatus in a defined manner. In this way it can be ensured that all the components are precisely uniformly irradiated during the period of time dt23 in which containers are still located in the apparatus. From the time t5 onwards, the transport device of the filling apparatus 1 is again slowed.

The synchronization of the transport speed during the period of time dt23 takes place by servo motor-controlled matching to the speed of the sterilization device ("on-the-fly").

All of the features disclosed in the application documents are claimed as essential to the invention in so far as they are novel individually or in combination with respect to the prior art.

The invention claimed is:

1. An apparatus for filling containers, comprising an entrance through which empty open containers can be introduced into the apparatus, comprising at least one transport device which conveys the containers along a predefined transport path, and an exit via which filled containers can be discharged from the apparatus, wherein the speed at which the transport device conveys the containers is variable, and comprising at least one filling device which fills the containers at least partially with a liquid medium on the transport path between the entrance and the exit, wherein the apparatus comprises a housing and arranged in the interior of the housing is at least one sterilization device in the form of a β-radiation unit which sterilizes components of the apparatus, and in this way keeps the apparatus sterile, wherein the transport device comprises a transport carousel, on which there are arranged a plurality of filling devices, for filling containers with a beverage.

2. The apparatus according to claim 1, wherein the intensity of the at least one β-radiation unit is controllable.

3. The apparatus according to claim 2, wherein the apparatus comprises a control unit which is configured to control the intensity of the at least one β-radiation unit as a function of an operating parameter of the apparatus.

4. The apparatus according to claim 3, wherein the operating parameter is the transport speed of the transport device.

5. The apparatus according to claim 3, wherein the operating parameter of the apparatus is an open state of a barrier device for the containers which is provided upstream of the apparatus.

6. The apparatus according to claim 1, wherein the components are selected from a group of components which contains transport starwheels, fittings, gripping devices for the containers.

7. The apparatus according to claim 1, wherein the apparatus is arranged in a clean chamber and this clean chamber is filled with a gas selected from a group of gases which contains a noble gas, nitrogen, and sterilized air.

8. The apparatus according to claim 1, wherein a plurality of β-radiation units are provided which are arranged in a stationary manner.

9. Installation for treating containers, comprising an apparatus according to claim 1, and a sterilization device which is arranged upstream of this apparatus and which sterilizes the containers.

10. The installation according to claim 9, wherein the sterilization device comprises at least one conveying device which conveys the containers through the sterilization device.

11. The installation according to claim 10, wherein the transport device and the conveying device include drives that can be controlled independently of one another.

12. The installation according to claim 11, wherein the drive of the transport device can be synchronized with the drive of the conveying device.

13. The apparatus according to claim 1, wherein the β-radiation unit keeps the apparatus sterile during continuous operation.

14. The apparatus according to claim 1, wherein the β-radiation is arranged to not irradiate the containers with the β-rays.

15. The apparatus according to claim 1, wherein the β-radiation is arranged to only irradiate the components which treat the containers.

16. The apparatus according to claim 1, wherein β-radiation units are provided in regions of the transport device at which no containers are located at any point of time.

17. The apparatus according to claim 1, wherein the at least one sterilization device in the form of a β-radiation unit is arranged to direct β-radiation only at regions of the transport device along which no containers are conveyed, whereby to sterilize components of the apparatus, and in this way keep the apparatus sterile without contaminating the containers with β-radiation.

18. An apparatus for filling containers, comprising an entrance through which empty open containers can be introduced into the apparatus, comprising at least one transport device which conveys the containers along a predefined transport path, and an exit via which filled containers can be discharged from the apparatus, wherein the speed at which the transport device conveys the containers is variable, and comprising at least one filling device which fills the containers at least partially with a liquid medium on the transport path between the entrance and the exit, wherein the apparatus comprises a housing and arranged in the interior of the housing is at least one sterilization device in the form of a β-radiation unit arranged to direct β-radiation only at regions of the transport device along which no containers are conveyed, whereby to sterilize components of the apparatus, and in this way keep the apparatus sterile without contaminating the containers with β-radiation, wherein the β-radiation is arranged to not irradiate the containers with β-rays.

* * * * *